United States Patent
Hirano et al.

(10) Patent No.: US 9,696,331 B2
(45) Date of Patent: Jul. 4, 2017

(54) AUTOMATIC ANALYTICAL DEVICE AND METHOD

(75) Inventors: Masaaki Hirano, Tokyo (JP); Kazuhiro Nakamura, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 47 days.

(21) Appl. No.: 14/117,723

(22) PCT Filed: May 15, 2012

(86) PCT No.: PCT/JP2012/062408
§ 371 (c)(1),
(2), (4) Date: Dec. 3, 2013

(87) PCT Pub. No.: WO2012/157642
PCT Pub. Date: Nov. 22, 2012

(65) Prior Publication Data
US 2014/0093426 A1    Apr. 3, 2014

(30) Foreign Application Priority Data
May 16, 2011    (JP) .................................. 2011-109243

(51) Int. Cl.
*G01N 35/10*    (2006.01)

(52) U.S. Cl.
CPC ................................ *G01N 35/1011* (2013.01)

(58) Field of Classification Search
CPC ............. G01N 35/10; G01N 35/1002; G01N 35/1011; G01N 2035/0474
See application file for complete search history.

(56) References Cited

U.S. PATENT DOCUMENTS 5,215,714 A * 6/1993 Okada et al. ................... 422/64
5,443,791 A * 8/1995 Cathcart et al. ............... 422/65
(Continued)

FOREIGN PATENT DOCUMENTS

CN    101308155 A    11/2008
CN    101526542 A    9/2009
(Continued)

OTHER PUBLICATIONS

Chinese Office Action received in corresponding Chinese Application No. 201280023931.2 dated Jul. 25, 2014.
(Continued)

*Primary Examiner* — Brian R Gordon
(74) *Attorney, Agent, or Firm* — Mattingly & Malur, PC

(57) ABSTRACT

The device uses a dispensing probe; a dispensing probe drive mechanism having at least one rotation drive shaft as a horizontal drive mechanism for the dispensing probe, a positioning member with a portion, which is contacted by the dispensing probe during positioning, is formed in a circular shape; a contact detection mechanism for detecting contact between the dispensing probe and the positioning member, and a control unit. The control unit drive-controls only one drive shaft into contact with the circular portion of the positioning member, and then drive-controls only one drive shaft other than the previously drive-controlled shaft into contact with the circular portion of the positioning member, and then calculates position information on a center point at a desired position where the dispensing probe is to be positioned, on the basis of position information on each point at which the contact has been detected, or the like.

1 Claim, 19 Drawing Sheets

(56) References Cited

U.S. PATENT DOCUMENTS

| | | | |
|---|---|---|---|
| 5,455,008 A * | 10/1995 | Earley et al. | 422/511 |
| 5,635,364 A * | 6/1997 | Clark et al. | 435/7.92 |
| 5,646,049 A * | 7/1997 | Tayi | 436/518 |
| 6,270,726 B1 * | 8/2001 | Tyberg et al. | 422/509 |
| 2002/0095974 A1 | 7/2002 | Gilson et al. | |
| 2002/0178779 A1 | 12/2002 | Gilson et al. | |
| 2004/0096368 A1 | 5/2004 | Davis et al. | |
| 2004/0265173 A1 * | 12/2004 | Matsumoto et al. | 422/64 |
| 2006/0062692 A1 * | 3/2006 | Tokieda | G01N 35/0099 422/64 |
| 2007/0065945 A1 | 3/2007 | Sigrist | |
| 2009/0226344 A1 | 9/2009 | Nishida et al. | |
| 2010/0250010 A1 | 9/2010 | Ferrara et al. | |
| 2013/0078617 A1 * | 3/2013 | Ueda et al. | 435/5 |
| 2013/0243653 A1 * | 9/2013 | Koiso et al. | 422/68.1 |
| 2014/0178251 A1 * | 6/2014 | Yamada et al. | 422/67 |

FOREIGN PATENT DOCUMENTS

| | | |
|---|---|---|
| JP | 2000-146548 A | 5/2000 |
| JP | 2001-091522 A | 4/2001 |
| JP | 2003-322656 A | 11/2003 |
| JP | 2005-181135 A | 7/2005 |
| JP | 2005-531769 A | 10/2005 |
| JP | 2007-086073 A | 4/2007 |
| JP | 2007-139704 A | 6/2007 |
| JP | 3996851 B2 | 8/2007 |
| JP | 2007-285957 A | 11/2007 |
| JP | 2008-256566 A | 10/2008 |
| JP | 2009-063448 A | 3/2009 |
| JP | 2009-210373 A | 9/2009 |
| JP | 2009-300152 A | 12/2009 |
| JP | 2010-091469 A | 4/2010 |
| WO | 2010/110872 A1 | 9/2010 |

OTHER PUBLICATIONS

Journal of Optoelectronics Laser; vol. 17, No. 5, May 2006.
European Search Report received in corresponding European Application No. 12785409 dated Sep. 29, 2014.
Lin Wen Huan et al., "2.3 Plane Coordinates Computation of Engineering Survey; 2.3.1 Center Coordinates Computation of Three-point Circumcircle", Dec. 31, 1978.
Duan Xiao Wu, "Center of Circumcircle", Aug. 31, 2002.

* cited by examiner

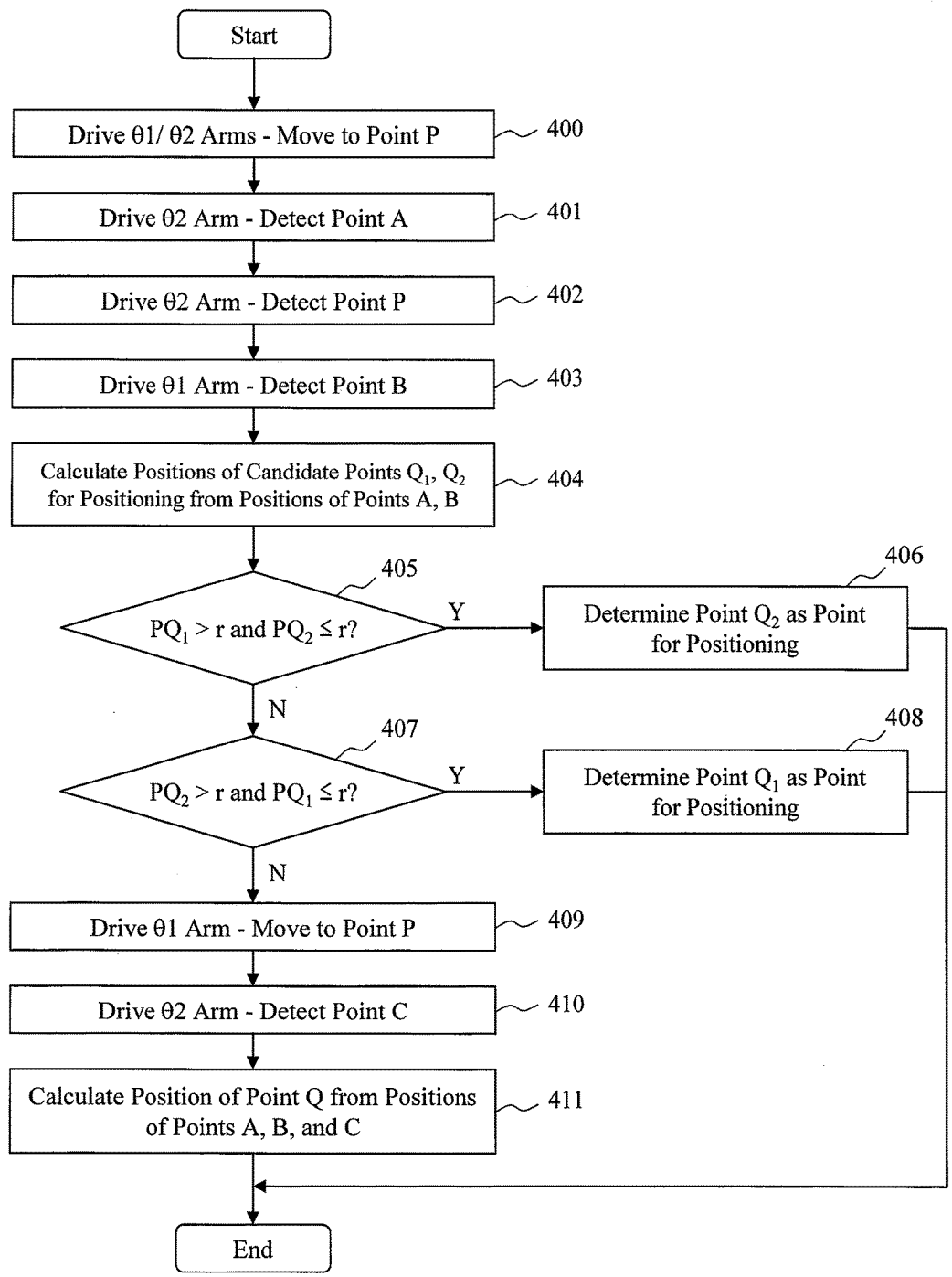

AUTOMATIC ANALYTICAL DEVICE AND METHOD

TECHNICAL FIELD

The present invention relates to an automatic analytical device with a dispensing drive mechanism.

BACKGROUND ART

Conventionally, there have been provided an automatic analytical device that can perform positioning of a sample probe or a reagent probe with high accuracy (see Patent Literature 1). Patent Literature 1 describes providing an automatic analytical device with a detection unit that detects proximity or contact of a probe to/with a solid or a liquid. In addition, Patent Literature 1 also describes attaching a jig, which has a center position detection portion that can detect the center position of a reaction container, to the reaction container. Further, Patent Literature 1 describes that whether or not the probe that is moving has come into proximity to or has come into contact with the center position detection portion of the jig is detected with the detection unit, whereby the probe is positioned at the center of the reaction container.

There has been also provided a probe drive system that determines the position of each probe tip by driving the probe tip into contact with a point on the side wall of a locator well and sensing the contact (see Patent Literature 2).

CITATION LIST

Patent Literature

Patent Literature 1: JP 2009-300152 A
Patent Literature 2: JP 3996851 B

SUMMARY OF INVENTION

Technical Problem

Patent Literature 1 describes a method of automatically positioning a probe at a stop position using a dispensing drive mechanism that has a two-dimensional horizontal movement mechanism including a rotation drive shaft. This method, however, involves sequentially checking whether or not a place that may possibly become a stop position is located at the center position of the reaction container. Thus, the number of steps required for the check is large.

Patent Literature 2 describes a method of automatically positioning a probe tip using a probe drive system that has a two-dimensional horizontal movement mechanism with only a linear drive shaft. This method, however, involves driving each probe along each linear drive shaft to detect contact between the probe and a point on the side wall of the cylindrical locator well, and determining an intermediate point between contact points as the center point in each drive shaft direction. Therefore, this method is not applicable to positioning of a probe with a dispensing drive mechanism that includes rotation drive.

It is an object of the present invention to provide an automatic analytical device capable of automatically position a probe in a short time, using a dispensing drive mechanism having a two-dimensional horizontal movement mechanism including at least one rotation drive shaft.

Solution to Problem

As an example to solve the aforementioned problem, the present invention has the following features:

(1) a dispensing probe that dispenses a predetermined amount of a sample or a reagent;

(2) a dispensing drive mechanism with two or more drive shafts for two-dimensionally moving the dispensing probe in the horizontal direction (note that at least one of the drive shafts is a rotation drive shaft);

(3) a positioning member that can be set or is arranged at at least one of a suction position, a discharge position, or a cleaning position of the dispensing probe (a portion of the positioning member that is contacted by the dispensing probe when positioning is performed is formed in a circular shape that has a position for positioning as the center);

(4) a contact detection mechanism that detects contact between the dispensing probe and the positioning member; and (5) a control unit that drive-controls only one of the two or more drive shafts of the dispensing probe drive mechanism into contact with the circular portion of the positioning member, and then drive-controls only one drive shaft other than the previously drive-controlled drive shaft into contact with the circular portion of the positioning member, and further performs, on the basis of position information on each point at which the contact has been detected, or on the basis of position information on each point at which the contact has been detected and information on a movement trajectory of the dispensing probe, calculation of position information on the center point of at least one of the suction position, the discharge position, or the cleaning position of the dispensing probe.

Advantageous Effects of Invention

According to the present invention, it is possible to, even when an automatic analytical device has mounted thereon a dispensing drive mechanism with two or more drive shafts for two-dimensional movement, and at least one of the drive shafts is a rotation drive shaft, automatically position a dispensing probe at a predetermined position through a smaller number of steps and in a shorter time than with the conventional devices.

Other problems, structures, and advantageous effects will become apparent from the following description of embodiments.

BRIEF DESCRIPTION OF DRAWINGS

FIG. 8 is a flowchart illustrating a positioning process that is performed based on a plurality of contact points and the movement trajectory of a dispensing probe;

DESCRIPTION OF EMBODIMENTS

Hereinafter, embodiments of the present invention will be described with reference to the drawings. It should be noted that the embodiments of the present invention are not limited to those described below, and various variations are possible within the scope and spirit of the present invention.

Embodiment 1

This embodiment will describe an example in which, when a dispensing drive mechanism has two rotation drive shafts, positioning of a dispensing probe is performed through detection of a plurality of contact points.

Figure 1:
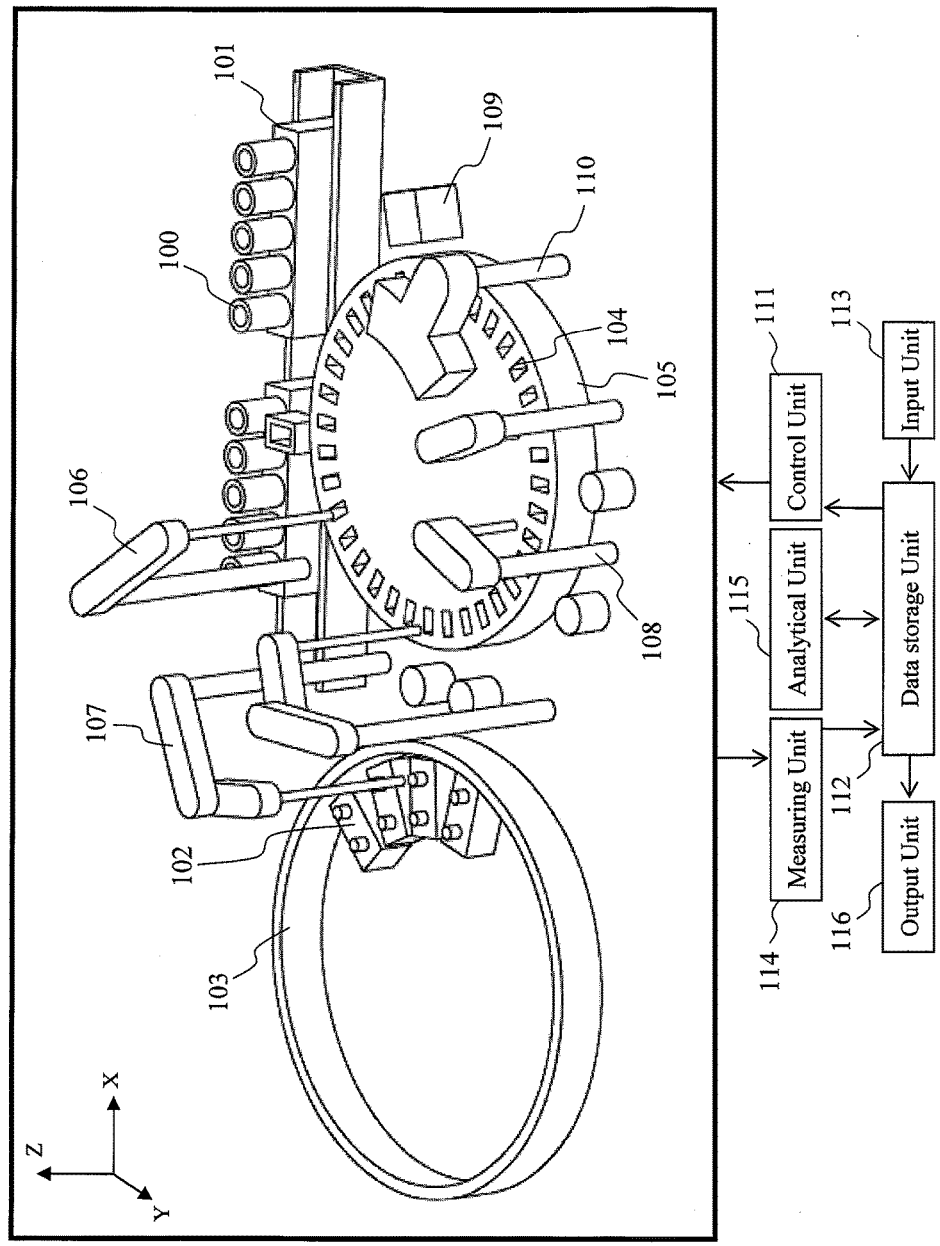
FIG. 1 is a view showing the overall structure of an automatic analytical device in accordance with an embodiment.

FIG. 1 shows an exemplary overall configuration of an automatic analytical device. The automatic analytical device includes a sample cup 100 that holds a sample, a sample rack 101 having a plurality of sample cups 100 arranged thereon, a reagent bottle 102 that holds a reagent, a reagent disc 103 having a plurality of reagent bottles 102 arranged thereon, a cell 104 in which a sample and a reagent are mixed to obtain a reaction solution, a cell disc 105 having a plurality of cells 104 arranged thereon, a sample dispensing mechanism 106 that can move a predetermined amount of a sample from the sample cup 100 into the cell 104, a reagent dispensing mechanism 107 that can move a predetermined amount of a reagent from the reagent bottle 102 into the cell 104, an agitation unit 108 that agitates and mixes the sample and the reagent in the cell 104, a measuring unit 109 that irradiates the reaction solution in the cell 104 with light and receives light obtained thereby, a cleaning unit 110 that cleans the cell 104, a control unit 111 that controls each portion of the device, a data storage unit 112 that stores various data, an input unit 113 that can input data that is necessary to the data storage unit 112 from the outside, a measuring unit 114 that calculates up to absorbance from the amount of light obtained with the measuring unit 109, an analytical unit 115 that identifies the amounts of components from the absorbance, and an output unit 116 that can display data and output the data to the outside.

Each of the reagent disc 103 and the cell disc 105 is in the shape of a disc, and is rotation-driven about the rotation axis. It should be noted that the reagent disc 103 and the cell 104 are arranged at around the circumferential positions of the reagent disc 103 and the cell disc 105, respectively.

The amounts of components of a sample are analyzed through the following procedures. First, a predetermined amount of a sample in the sample cup 100 is dispensed into the cell 104 by the sample dispensing mechanism 106. Next, a predetermined amount of a reagent in the reagent bottle 102 is dispensed into the cell 104 by the reagent dispensing mechanism 107. Then, the sample and the reagent in the cell 104 are agitated by the agitation unit 108 to obtain a reaction solution. If necessary, a plurality of reagents are additionally dispensed into the cell 104 using the reagent dispensing mechanism 107. In dispensing, the sample cup 100, the reagent bottle 102, and the cell 104 are moved to predetermined positions through transfer of the sample rack 101 and rotation of the reagent disc 103 and the cell disc 105. When the reaction is complete, the inside of the cell 104 is cleaned by the cleaning unit 110, and the next analysis is performed. The absorbance of the reaction solution is measured by the measuring unit 109 and the measuring unit 114, and is then stored in the data storage unit 112 as the absorbance data.

The stored absorbance data is analyzed by the analytical unit 115 on the basis of calibration curve data and the Lambert-Beer's law. Such analysis enables analysis of the amount of components contained in the sample. Data that is necessary for the control of each portion/analysis is input to the data storage unit 112 from the input unit 113. Various data and analysts results are displayed by and/or output from the output unit 116.

Figure 2:
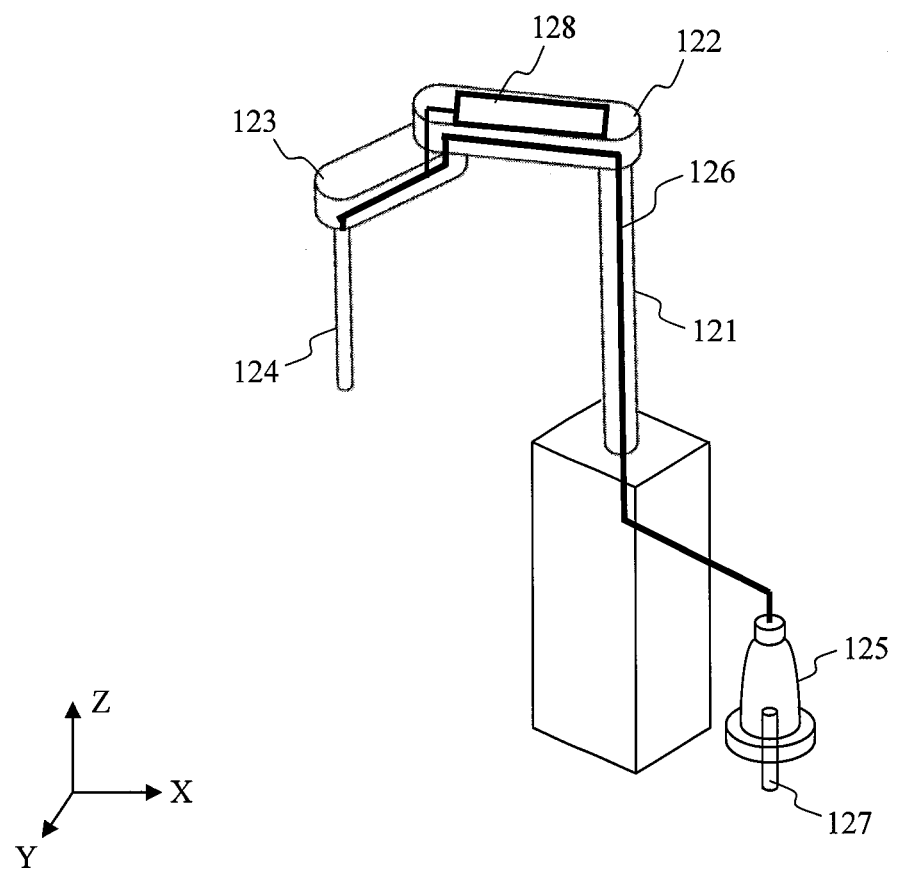
FIG. 2 is a view showing an exemplary structure of a dispensing drive mechanism.

FIG. 2 is a view showing an exemplary structure of the dispensing drive mechanism used in this embodiment. In this embodiment, an end portion of a θ1 arm 122 is rotatably attached to an upper end position of a shaft 121, which can be driven up and down, in the XY plane. In addition, an end portion of a θ2 arm 123 is rotatably attached to a tip position, which is a free end, of the θ1 arm 122, in the XY plane. Further, a dispensing probe 124 is attached to a tip position, which is a free end, of the θ2 arm 123 such that it extends downward in the Z-axis direction.

The dispensing probe 124 and a syringe 125 are connected via a tube 126. The tube 126 passes through the shaft 121, the θ1 arm 122, and the θ2 arm 123 from a base of the shaft 121, and is connected to one end of the dispensing probe 124. The syringe 125 has movably attached thereto a plunger 127 for changing the inner volume of the syringe 125. A sample or a reagent is suctioned into or discharged from the tip of the dispensing probe 124 in accordance with the movement position of the plunger 127. In addition, a capacitive liquid level detector 128 is connected to the dispensing probe 124, and can detect that the dispensing probe 124 has come into contact with a sample, a reagent, or metal.

Figure 3A:
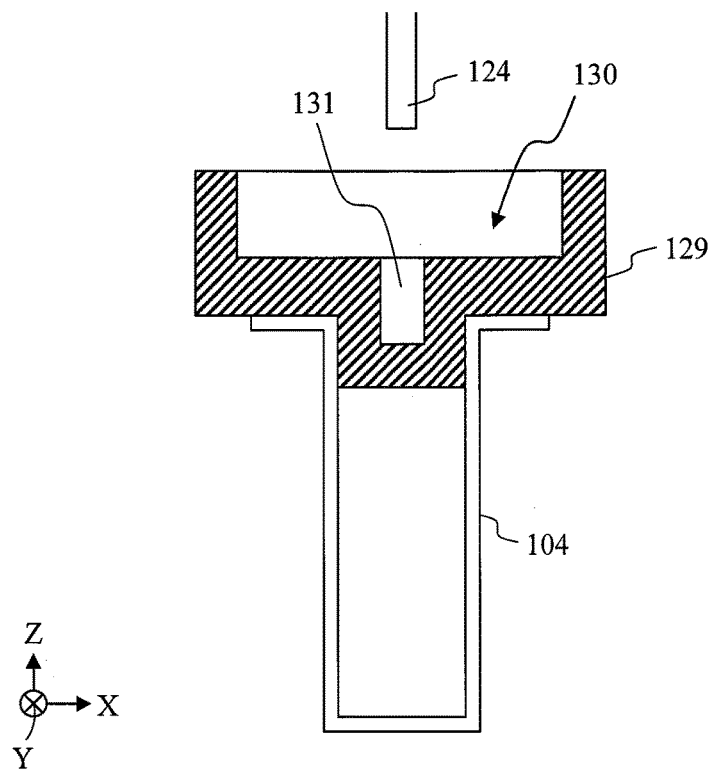
FIG. 3A is a view showing an exemplary cross-sectional structure of a positioning member.
Figure 3B:
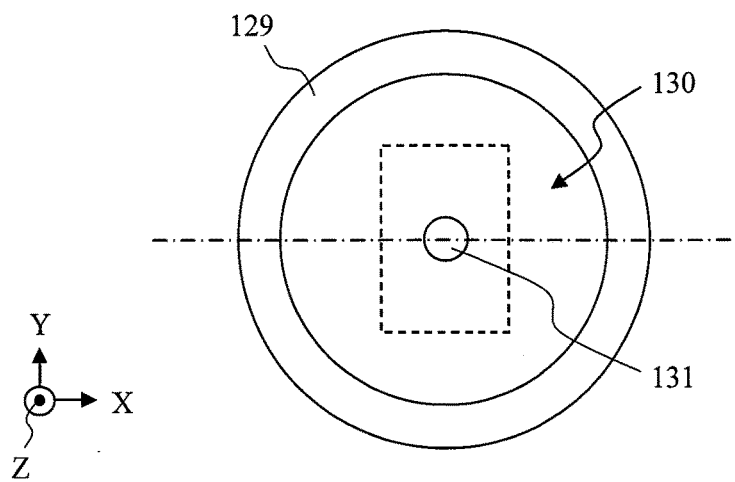
FIG. 3B is a view showing a top surface structure of the positioning member.

FIGS. 3A and 3B show an exemplary structure of a positioning member 129. FIG. 3A shows a cross-sectional structure of the positioning member 129 and the cell 140 to which the positioning member 129 is attached, and FIG. 3B shows a top view of the positioning member 129. The positioning member 129 is a jig that can be attached to or detached from an opening portion of the cell 104. The shape of a portion, which is attached to the cell 104, of the positioning member 129 may be any shape as long as it allows attachment to the cell 104. In this embodiment, a cylindrical structure 130 is provided on an upper end side of the positioning member 129 in the attached state. Herein, the cylindrical structure 130 is formed such that its central axis coincides with the target point for positioning.

Although an example of an attachable/detachable jig is described herein, the positioning process proposed in this specification can be realized even when a similar structure is formed in advance at a place where the reagent bottle 102 of the reagent disc 103, for example, is to be provided.

The positioning member 129 is made of metal. Thus, contact with the dispensing probe 124 can be detected with the liquid level detector 128. In this embodiment, contact between the dispensing probe 124 and the inner surface of the cylindrical structure 130 is detected, and positioning of the dispensing probe 124 is performed on the basis of position information thereon. Therefore, the cylindrical structure 130 desirably has a size that allows, even when there is a processing error or an assembling error, the dispensing probe 124 to be always positioned within the cylinder when the dispensing probe 124 is moved to the initial reference position.

Although this embodiment will describe an example in which contact is detected capacitively, it is also possible to detect contact between the positioning member 129 and the dispensing probe 124 by connecting the two members to an electrical conduction detector (not shown) in advance, and detecting electrical conduction when they come into contact with each other.

In addition, it is also possible to, as shown in FIGS. 3A and 3B, form a dent 131 at the center portion of the cylindrical structure 130. The dent 131 is used as a positioning checking jig with an inner diameter that is greater than the outer diameter of the dispensing probe 124. For example, it is possible to, after the positioning process described below, lower the dispensing probe 124 down to a position that has been calculated as a target point and check if the dispensing probe 124 has been inserted into the dent 131, thereby detecting if the dispensing probe 124 has been correctly positioned.

Figure 4:
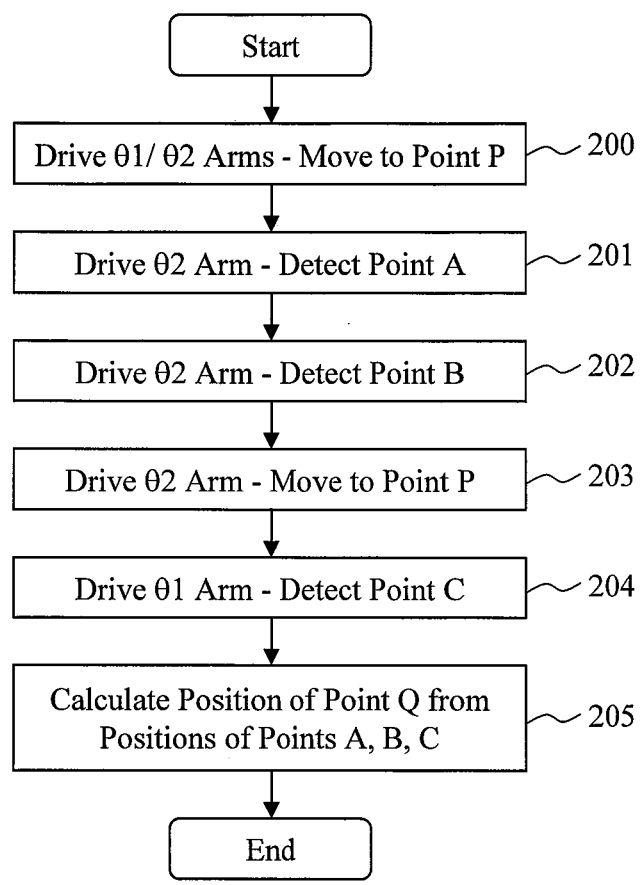
FIG. 4 is a flowchart illustrating a positioning process that uses a plurality of contact points when the dispensing drive mechanism has two rotation drive shafts.

Next, a positioning method in accordance with this embodiment will be described with reference to FIGS. 4 and 5A to 5E. That is, a positioning method using a dispensing drive mechanism that has mounted thereon a horizontal movement mechanism with two rotation drive shafts will be described. Herein, FIG. 4 is a flowchart showing a summary of the method of the positioning process in accordance with this embodiment. FIGS. 5A to 5E show the positional relationship among the θ1 arm 122, the θ2 arm 123, and the cylindrical structure 130 in the positioning process. The positioning process is executed by the control unit 111.

Figure 5A:
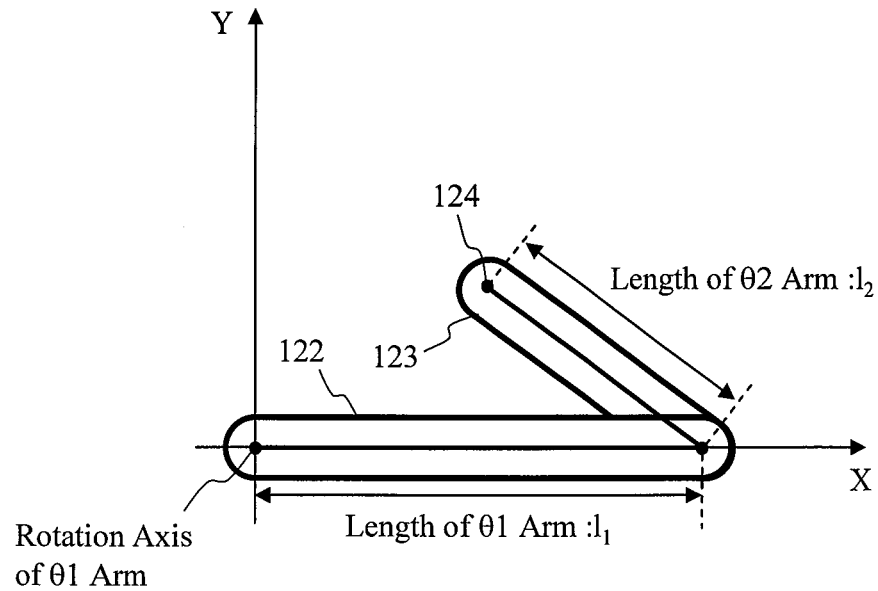
FIG. 5A is a view illustrating a step of the positioning process that uses a plurality of contact points when the dispensing drive mechanism has two rotation drive shafts.

FIG. 5A shows the coordinate system used in the following description and the initial position and dimensions of each arm. As shown, the rotation axis of the θ1 arm 122 is the origin of the coordinates, and the axis direction of the θ1 arm 122 at the home position (i.e., initial position) is the X-axis. It should be noted that the axis direction that is perpendicular to the-X axis is the Y-axis. It should also be noted that the arm length of the θ1 arm 122 is $l_1$, and the arm length of the θ2 arm 123 is $l_2$.

Figure 5B:
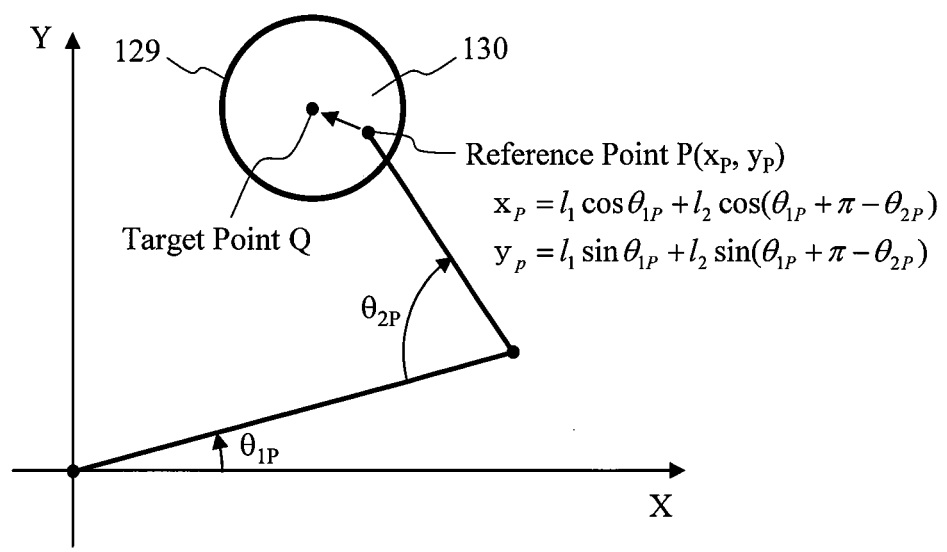
FIG. 5B is a view illustrating a step of the positioning process that uses a plurality of contact points when the dispensing drive mechanism has two rotation drive shafts.

The angle of each arm after the dispensing probe 124 is moved can be determined from the initial angles of the θ1 arm 122 and the θ2 arm 123 before they are driven, the number of pulses of each movement that provides the amount of movement with respect to the initial angle (i.e., the amount of rotation), and movement angular resolution. In addition, the coordinate positions (x,y) of the dispensing probe 124 after the movement can be determined from the length of each arm and the angle of each arm as shown in FIG. 5B. In the following steps, the position coordinates of the dispensing probe 124 after the movement can be determined similarly. Calculation of the coordinate positions is executed by the control unit 111.

First, as shown in FIG. 5B, the dispensing probe 124 is moved from the initial position to a predetermined reference point P (process 200). Herein, the reference position P is a stop position for when there is no processing error or assembling error due to the production of the parts. Horizontal movement of the dispensing probe 124 is realized by rotation drive of the θ1 arm 122 and the θ2 arm 123 in the XY plane. When the dispensing probe 124 is positioned at the coordinate positions of the reference point P, the control unit 111 lowers the shaft 121. The amount of lowering is down to a height at which the tip portion of the dispensing probe 124 can contact the inner surface of the cylindrical structure 130 of the positioning member 129 when the dispensing probe 124 is moved in the XY plane after it is lowered.

The reference point P is originally expected to coincide with a target point Q for positioning. However, the target point Q for positioning may not coincide with the target point P due to a processing error or an assembling error. In such a case, positioning of the dispensing drive mechanism should be reset.

Figure 5C:
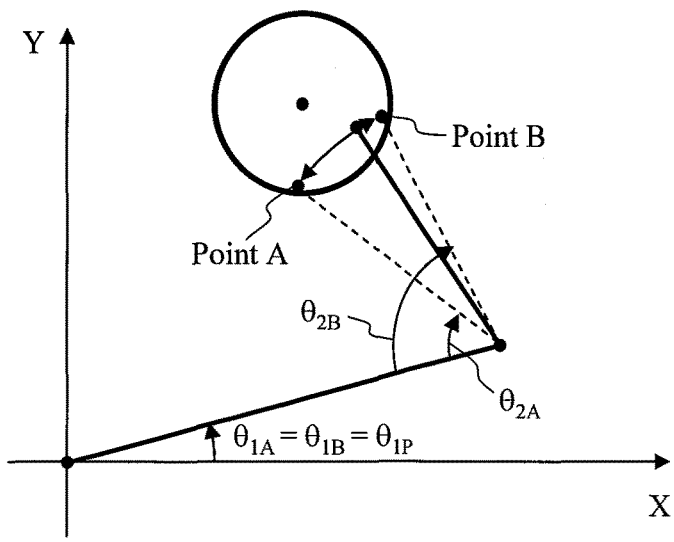
FIG. 5C is a view illustrating a step of the positioning process that uses a plurality of contact points when the dispensing drive mechanism has two rotation drive shafts.

Thus, as shown in FIG. 5C, only the θ2 arm 123 is rotation-driven in the right and left directions in the XY plane so that the dispensing probe 124 is made into contact with the inner surface of the cylindrical structure 130 of the positioning member 129. In FIG. 5C, a contact point located on the left side is indicated by a point A, and a contact point located on the right side is indicated by a point B. Then, each time contact is detected, the coordinates $(x_a, y_a)$ and $(x_b, y_b)$ of the points A and B are calculated (processes 201 and 202).

It should be noted that the control unit 111 can, by confirming contact with the point A, confirm that the positioning member 129 is attached and that the liquid level detector 128 is operating normally. If contact with the point A cannot be confirmed, the control unit 111 stops the positioning operation without executing the following operation. In that case, the operator is desirably informed that the positioning operation has been stopped through the output unit 116.

When the coordinates of the points A and B are detected as described above, only the θ2 arm 123 is driven again, and the dispensing probe 124 is returned to the position of the reference point P (process 203). This process is not always necessary. However, calculating the coordinates of a point C to be detected next from the reference point P, which is the initial position, can increase the calculation accuracy for the coordinates of the point C.

Figure 5D:
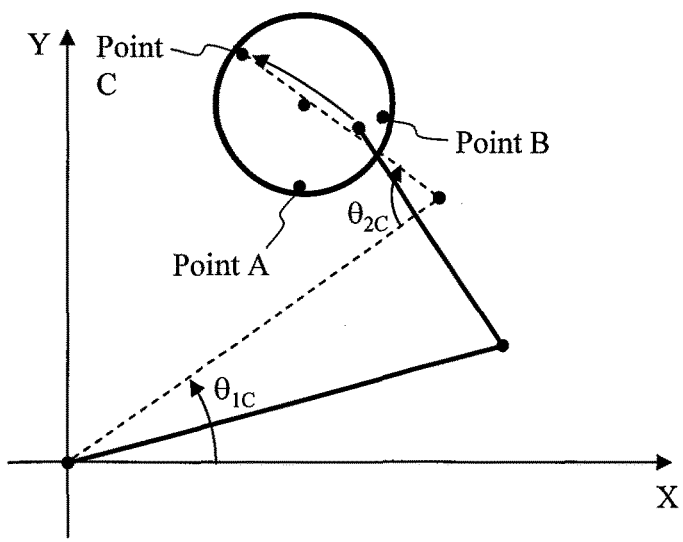
FIG. 5D is a view illustrating a step of the positioning process that uses a plurality of contact points when the dispensing drive mechanism has two rotation drive shafts.

When the dispensing probe 124 has returned to the reference point P, as shown in FIG. 5D, only the θ1 arm 122 is rotation-driven to move the dispensing probe 124 to a position at which the dispensing probe 124 contacts the inner surface of the cylindrical structure 130 of the positioning member 129. In this case, the dispensing probe 124 is also movable in two directions. In this embodiment, the dispensing probe 124 is driven such that it is moved in a direction opposite to a direction in which the points A and B are present, that is, the dispensing probe 124 is moved away from the points A and B. At this time, a point at which the contact is detected is indicated by a point C (process 204). The control unit 111 calculates the coordinates $(x_c, y_c)$ of the point C as with the cases of the points A and B.

Through detection of the contact points (the points A to C), the coordinates of the respective points $(x_a, y_a)$ to $(x_c, y_c)$ are calculated by the control unit 111. The points A to C are points on the circumference of a circle (more correctly, an inner side than the inner wall of the positioning member 129 by the radius of the dispensing probe 124). Therefore, the coordinates of the target point Q, which is the center of the circle on the circumference corresponding to the inner wall surface of the positioning member 129, can be calculated from the three points through computation (process 205). The target point Q provides the coordinate positions at which the dispensing probe 124 should be positioned.

Figure 5E:
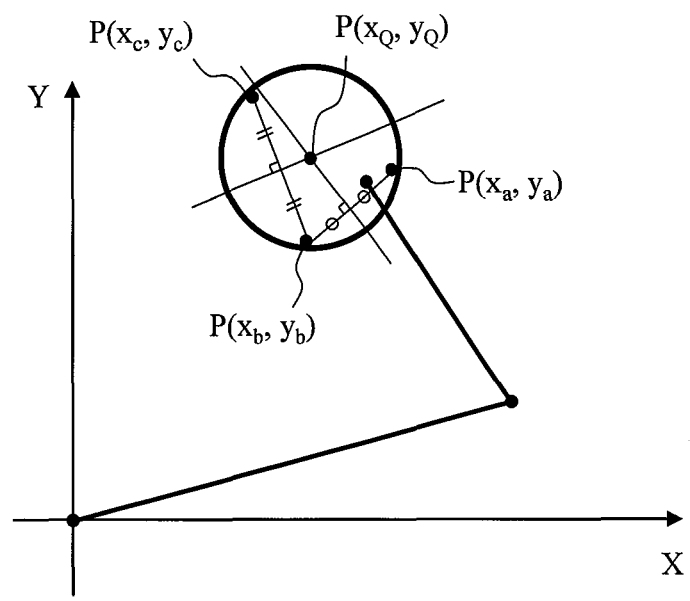
FIG. 5E is a view illustrating a step of the positioning process that uses a plurality of contact points when the dispensing drive mechanism has two rotation drive shafts.

The coordinates of the target point Q can be calculated by, as shown in FIG. 5E, selecting two pairs of any two points from the points A to C and determining an intersection point between perpendicular bisectors thereof. Formulae of the perpendicular bisectors can be given by the following formulae.

$$y = -\frac{x_b - x_a}{y_b - y_a}\left(x - \frac{x_a + x_b}{2}\right) + \frac{y_a + y_b}{2} \qquad \text{[Formula 1]}$$

-continued
$$y = -\frac{x_c - x_a}{y_c - y_a}\left(x - \frac{x_a + x_c}{2}\right) + \frac{y_a + y_c}{2}$$

When the two formulae are simultaneously solved, the coordinates of the point Q $(x_Q, y_Q)$ can be calculated by the following formulae.

$$x_Q = \frac{\{(x_b^2 - x_a^2 + y_b^2 - y_a^2)(y_c - y_a) - (x_c^2 - x_a^2 + y_c^2 - y_a^2)(y_b - y_a)\}}{2\{(x_b - x_a)(y_c - y_a) - (x_c - x_a)(y_b - y_a)\}} \qquad \text{[Formula 2]}$$

$$y_Q = \frac{\{(x_b^2 - x_a^2 + y_b^2 - y_a^2)(x_c - x_a) - (x_c^2 - x_a^2 + y_c^2 - y_a^2)(x_b - x_a)\}}{2\{(y_b - y_a)(x_c - x_a) - (y_c - y_a)(x_b - x_a)\}}$$

Alternatively, it is also possible to determine the center of a circle that constitutes the inner side of the cylindrical structure 130 by using the method of least squares. In such a case, the circumference of the circle can be represented by the following formula, using the coordinates $(x_Q, y_Q)$ of the center point (point Q).

$$(x - x_Q)^2 + (y - y_Q)^2 = r^2 \qquad \text{[Formula 3]}$$

Herein, $x_Q$ and $y_Q$ that minimize S in the following formula are determined $$S = \sum\{(x_i - x_Q)^2 + (y_i - y_Q)^2 - r^2\}^2 \qquad \text{[Formula 4]}$$
$$= \sum(x_i^2 - 2x_i x_Q + x_Q^2 + y_i^2 - 2y_i y_Q + y_Q^2 - r^2)^2$$
$$(i = A, B, C, \ldots)$$

Herein, provided that $\alpha = -2x_Q$, $\beta = -2y_Q$, and $\gamma = x_Q^2 + y_Q^2 - r^2$, S in the previous formula can be represented by the following formula.

$$S = \sum(x_i^2 + \alpha x_i + y_i^2 + \beta y_i + \gamma)^2 \qquad \text{[Formula 5]}$$

$$\frac{\partial S}{\partial \alpha} = 2\left(\alpha \sum x_i^2 + \beta \sum x_i y_i + \gamma \sum x_i + \sum(x_i^3 + x_i y_i^2)\right)$$

$$\frac{\partial S}{\partial \beta} = 2\left(\alpha \sum x_i y_i + \beta \sum y_i^2 + \gamma \sum y_i + \sum(x_i^2 y_i + y_i^3)\right)$$

$$\frac{\partial S}{\partial \gamma} = 2\left(\alpha \sum x_i + \beta \sum y_i + \gamma \sum 1 + \sum(x_i^2 + y_i^2)\right)$$

Further, the following formula is satisfied.

$$\text{Provided that } \frac{\partial S}{\partial \alpha} = 0, \frac{\partial S}{\partial \beta} = 0, \frac{\partial S}{\partial \gamma} = 0 \qquad \text{[Formula 6]}$$

$$\begin{pmatrix} \alpha \\ \beta \\ \gamma \end{pmatrix} = \begin{pmatrix} \sum x_i^2 & \sum x_i y_i & \sum x_i \\ \sum x_i y_i & \sum y_i^2 & \sum y_i \\ \sum x_i & \sum y_i & \sum 1 \end{pmatrix}^{-1} \begin{pmatrix} -\sum(x_i^3 + x_i y_i^2) \\ -\sum(x_i^2 y_i + y_i^3) \\ -\sum(x_i^2 + y_i^2) \end{pmatrix}$$

When the matrix is solved and defining formulae of $\alpha$ and $\beta$ are applied, the following relationship is calculated.

$$x_Q = -\alpha/2, y_Q = -\beta/2, r = \sqrt{x_Q^2 + y_Q^2 - \gamma} \qquad \text{[Formula 7]}$$

That is, the coordinates $(x_Q, y_Q)$ of the point Q and the radius of the cylinder of the positioning member 129 are calculated. It should be noted that when the coordinates of the calculated point Q are substituted into the two formulae in FIG. 5B and $\theta_{1Q}$ and $\theta_{2Q}$ are solved, the angle between the θ1 arm 122 and the corresponding reference position and the angle between the θ2 arm 123 and the corresponding reference position can be calculated. The control unit 111 drives drive portions (e.g., motors) of the θ1 arm 122 and the θ2 arm 123 on the basis of the calculated $\theta_{1Q}$ and $\theta_{2Q}$, and positions them at the target point Q.

Herein, if the design values and the calculation results of the coordinates of the point Q or the radius of the cylinder of the positioning member greatly differ due to erroneous operations of the liquid level detector 128 or arrangement failures of the positioning member 129, the control unit 111 desirably outputs an alarm from the output unit 116 of the automatic analytical device to promote the operator to perform check.

With the aforementioned processing function mounted, it is possible to, even when the dispensing drive mechanism has two rotation drive shafts, automatically position the dispensing probe 124 at a predetermined position accurately and in a short time.

Embodiment 2

In Embodiment 1, horizontal drive of the dispensing probe 124 is realized by a combination of the two rotation drive shafts. However, this embodiment will describe a case where horizontal movement of the dispensing probe 124 is realized by a combination of a single linear drive shaft and a single rotation drive shaft.

Figure 6:
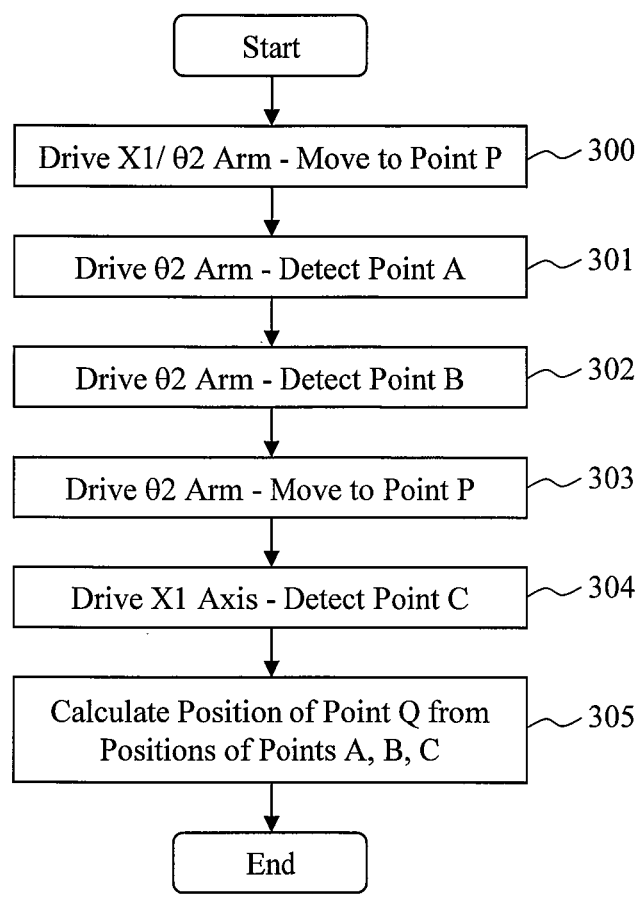
FIG. 6 is a flowchart illustrating a positioning process that uses a plurality of contact points when the dispensing drive mechanism has a linear drive shaft and a rotation drive shaft.

Hereinafter, a positioning method in accordance with this embodiment will be described with reference to FIGS. 6 and 7A to 7D. Herein, FIG. 6 is a flowchart showing a summary of the method of the positioning process in accordance with this embodiment. FIGS. 7A to 7D show the positional relationship among a linear stage 141, the θ2 arm 123, and the cylindrical structure 130 during the positioning process.

Figure 7A:
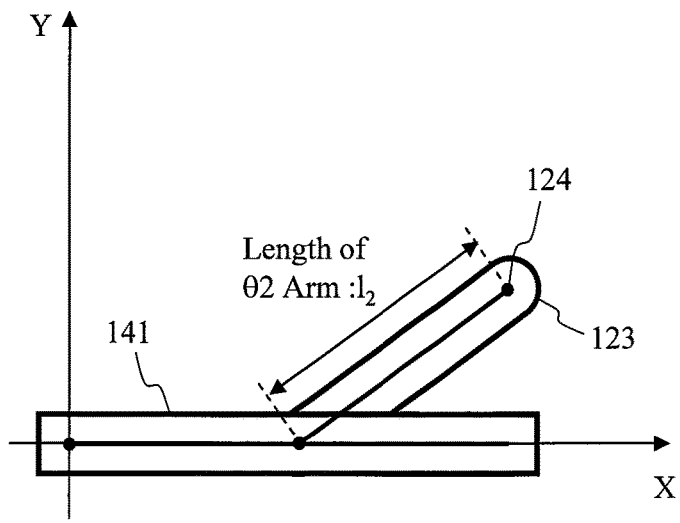
FIG. 7A is a view illustrating a step of the positioning process that uses a plurality of contact points when the dispensing drive mechanism has a linear drive shaft and a rotation drive shaft.

FIG. 7A shows the coordinate system used in the following description and the initial position and dimensions of each movable portion. In FIG. 7A, the X-axis of the coordinate system is made to coincide with the direction in which the linear stage 141 can move. The direction that is perpendicular to the X-axis is set as the Y-axis. The θ2 arm 123 is set on the linear stage 141, and the rotation drive shaft thereof is set on the X-axis. Attachment position of the rotation axis of the θ2 arm 123 is moved along with the movement of the linear stage 141 with respect to a linear guide (X-axis). The arm length of the θ2 arm 123 is $l_2$.

The position of the rotation axis of the θ2 arm 123 after the dispensing probe 124 is moved is given as the amount of movement (e.g., the number of pulses of movement) of the linear stage 141 with respect to the initial position (i.e., the origin of the X-axis). In addition, the angle of the θ2 arm 123 is given with the X-axis being the initial angle (=0°), and is given by the number of pulses of each movement that provides the amount of movement with respect to the initial angle (i.e., the amount of rotation) and movement angle resolution.

Figure 7B:
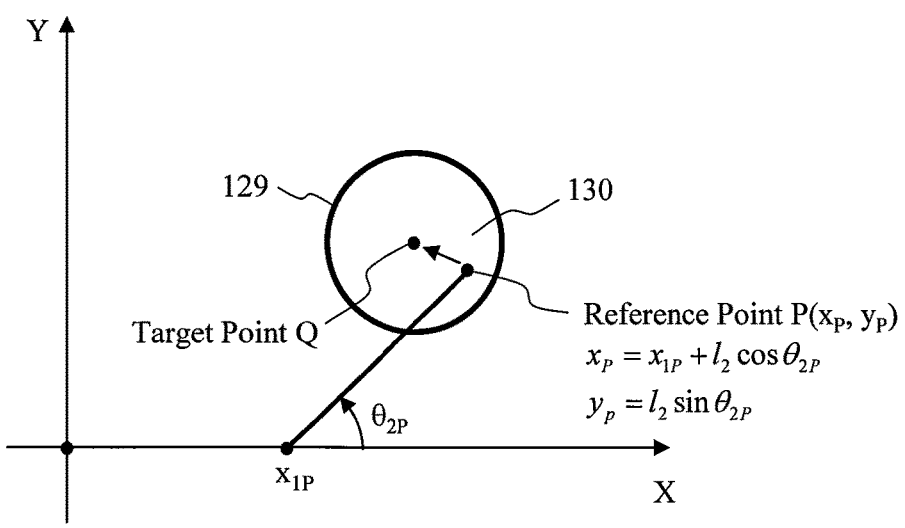
FIG. 7B is a view illustrating a step of the positioning process that uses a plurality of contact points when the dispensing drive mechanism has a linear drive shaft and a rotation drive shaft.

The coordinate positions (x,y) of the dispensing probe 124 after the movement can be determined from, as shown in FIG. 7B, the coordinate $x_{1P}$ of the rotation axis of the θ2 arm 123 on the X-axis and the angle $\theta_{2P}$ of the θ2 arm 123 with respect to the X-axis. In the following steps, the position coordinates of the dispensing probe 124 after the movement can be determined similarly. Calculation of the coordinate positions is executed by the control unit 111.

First, as shown in FIG. 7B, the dispensing probe 124 is moved from the initial position to a predetermined reference point P (process 300). Herein, the reference point P is a stop position for when there is no processing error or assembling error due to the production of the parts. Horizontal movement of the dispending probe 124 is realized by horizontal movement and rotational movement of the linear stage 141 and the θ2 arm 123, respectively, in the XY plane. When the dispensing probe 124 is positioned at the coordinate positions of the reference point P, the control unit 111 lowers the shaft 121. The amount of lowering is down to a height at which the tip portion of the dispensing probe 124 can contact the inner surface of the cylindrical structure 130 of the positioning member 129 when the dispensing probe 124 is moved in the XY plane after it is lowered.

In this case, the reference point P is also expected to coincide with a target point Q for positioning. However, the target point Q for positioning may not coincide with the reference point P due to a processing error or an assembling error. In such a case, positioning of the dispensing drive mechanism should be reset so that the reference point P coincides with the target point Q.

Figure 7C:
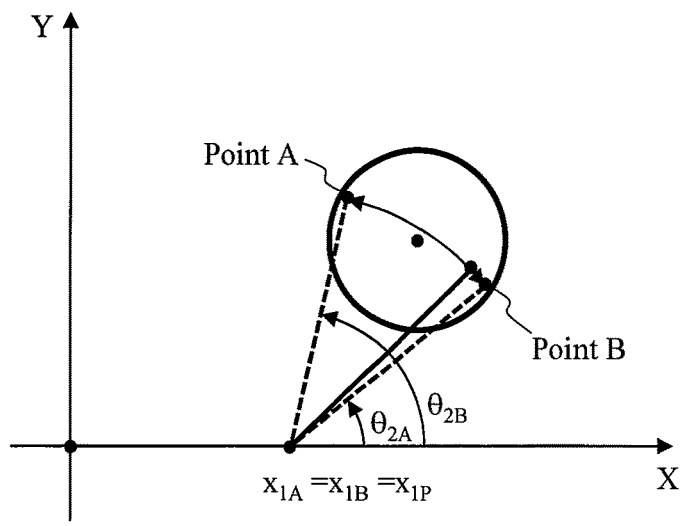
FIG. 7C is a view illustrating a step of the positioning process that uses a plurality of contact points when the dispensing drive mechanism has a linear drive shaft and a rotation drive shaft.

Thus, as shown in FIG. 7C, only the θ2 arm 123 is rotation-driven in the right and left directions in the XY plane, and the dispensing probe 124 is made into contact with the inner surface of the cylindrical structure 130 of the positioning member 129. In FIG. 7C, a contact point located on the left side is indicated by a point A, and a contact point located on the right side is indicated by a point B. Then, each time contact is detected, the coordinates $(x_a, y_a)$ and $(x_b, y_b)$ of the points A and B are calculated (processes 301 and 302).

It should be noted that the control unit 111 can, by confirming contact with the point A, confirm that the positioning member 129 is attached and that the liquid level detector 128 is operating normally. If contact with the point A cannot be confirmed, the control unit 111 stops the positioning operation without executing the following operation. In that case, the operator is desirably informed that the positioning operation has been stopped through the output unit 116.

When the coordinates of the points A and B are detected as described above, only the θ2 arm 123 is rotation-driven as in Embodiment 1, and the dispensing probe 124 is returned to the position of the reference point P (process 303). This process is not always necessary. However, calculating the coordinates of a point C to be detected next from the reference point P, which is the initial position, can increase the calculation accuracy for the coordinates of the point C.

Figure 7D:
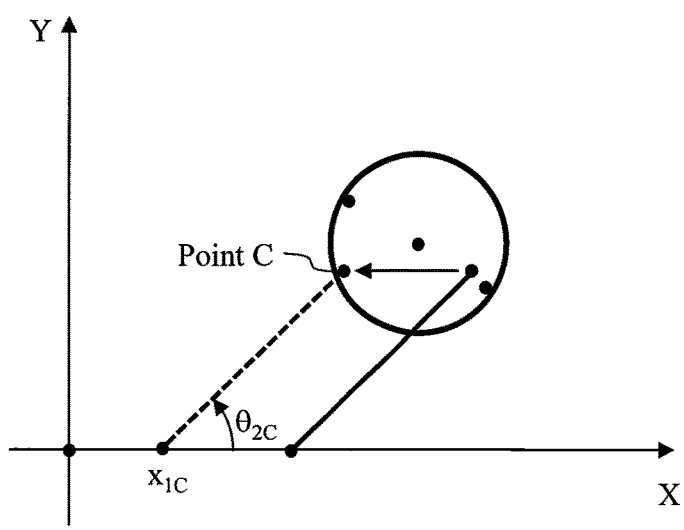
FIG. 7D is a view illustrating a step of the positioning process that uses a plurality of contact points when the dispensing drive mechanism has a linear drive shaft and a rotation drive shaft.

When the dispensing probe 124 has returned to the reference point P, as shown in FIG. 7D, only the linear stage 141 is driven linearly to move the dispensing probe 124 to a position at which the dispensing probe 124 contacts the inner surface of the cylindrical structure 130 of the positioning member 129. In this case, the dispensing probe 124 is also movable in two directions. In this embodiment, the dispensing probe 124 is driven such that it is moved in a direction in which, of the distance between the reference point P and the point A and the distance between the reference point P and the point B, a farther point is present. In FIG. 7D, the dispensing probe 124 is moved in the direction of the point A. At this time, a point at which the contact is detected is indicated by a point C (process 304). The control unit 111 calculates the coordinates $(x_c, y_c)$ of the point C as with the cases of the points A and B.

Through detection of the contact points (the points A to C), the coordinates of the respective points $(x_a, y_a)$ to $(x_c, y_c)$ are calculated by the control unit 111. The points A to C are points on the circumference of a circle (more correctly, an inner side than the inner wall of the positioning member 129 by the radius of the dispensing probe 124). Therefore, the coordinates of the point Q, which is the center of the circle on the circumference corresponding to the inner wall surface of the positioning member 129, can be calculated from the three points through computation (process 305). The point Q provides the coordinate positions at which the dispensing probe 124 should be positioned.

With the aforementioned processing function mounted, it is possible to, even when the dispensing drive mechanism has a single linear drive shaft and a single rotation drive shaft, automatically position the dispensing probe 124 at a predetermined position accurately and in a short time.

Embodiment 3

This embodiment will describe an example in which positioning is executed with not only contact points but also the movement trajectory of the dispensing probe 124 taken into consideration. It should be noted that the device configuration of the automatic analytical device is similar to that in Embodiment 1. That is, horizontal movement of the dispensing probe 124 is realized by a combination of two rotation drive shafts. Needless to say, the processing method described in this embodiment can also be applied to the automatic analytical device in accordance with Embodiment 2.

Hereinafter, the positioning method in accordance with this embodiment will be described with reference to FIGS. 8, 9A to 9D, and 10A to 10F. Herein, FIG. 8 is a flowchart of a positioning process that is performed based on contact points and the movement trajectory of the dispensing probe 124. Among the processing procedures shown in FIG. 8, conditional branch portions indicated by processes 405 and 407 correspond to the determination processes for which the movement trajectory of the dispensing probe 124 is taken into consideration, and thus it is determined if a candidate point that provides the target point Q can be determined at the determination time point. It should be noted that FIGS. 9A to 9D show a case where one of the candidate points for positioning can be determined as the target point Q by taking the movement trajectory of the dispensing probe 124 into consideration. FIG. 10 show a case where a candidate point for positioning cannot be determined as the target point Q even when the movement trajectory of the dispensing probe 124 is taken into consideration.

Figure 9A:
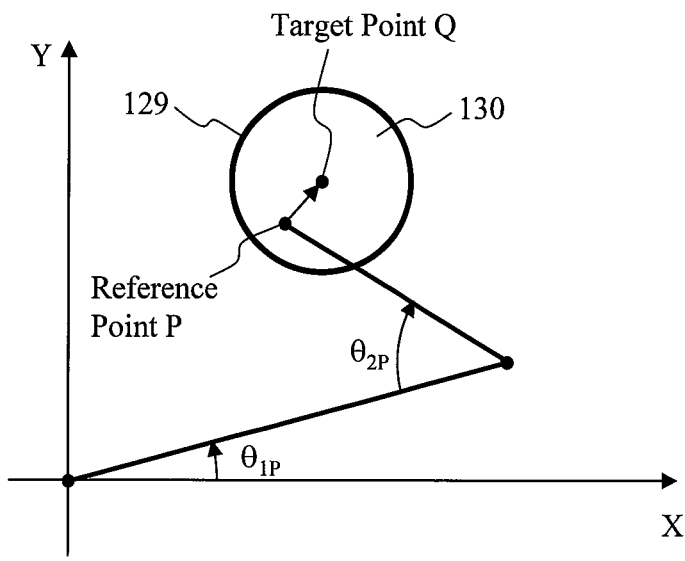
FIG. 9A is a view illustrating a step of the positioning process that is performed based on a plurality of contact points and the movement trajectory of a dispensing probe.

First, a case where a candidate point for positioning can be determined as the target point Q by taking the movement trajectory into consideration will be described. As shown in FIG. 9A, the θ1 arm 122 and the θ2 arm 123 are driven to move the dispensing probe 124 to the reference point P. After that, the shaft 121 is lowered down to a height at which the dispensing probe 124 can contact the inner surface of the cylindrical structure 130 of the positioning member 129 (process 400).

Figure 9B:
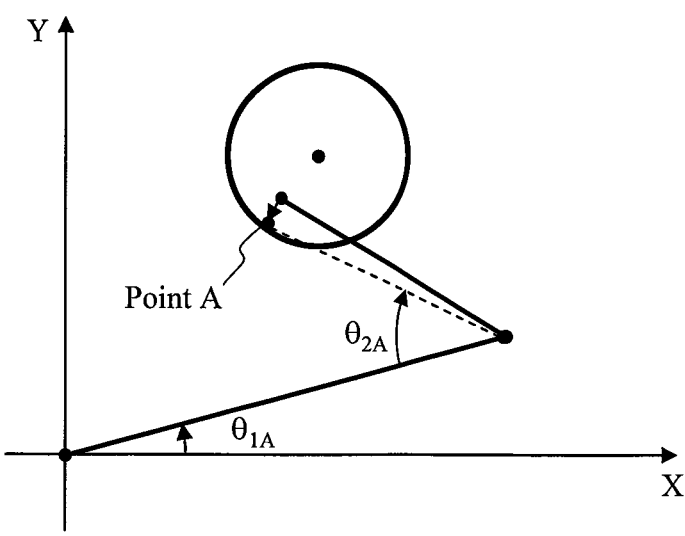
FIG. 9B is a view illustrating a step of the positioning process that is performed based on a plurality of contact points and the movement trajectory of a dispensing probe.

Next, as shown in FIG. 9B, only the θ2 arm 123 is rotation-driven in one direction, and the dispensing probe 124 is made into contact with the inner surface of the cylindrical member 130 that constitutes the positioning member 129, so that the position of a point A is detected (process 401).

After that, the θ2 arm 123 is rotation-driven in the opposite direction, and the dispensing probe 124 is returned to the position of the reference point P (process 402).

Figure 9C:
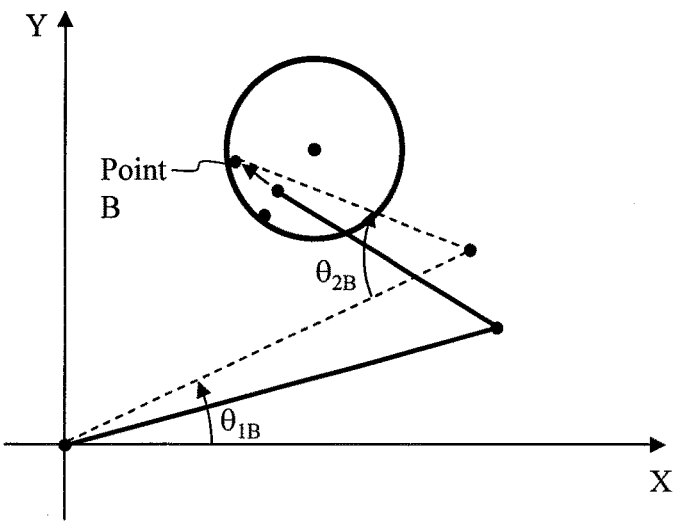
FIG. 9C is a view illustrating a step of the positioning process that is performed based on a plurality of contact points and the movement trajectory of a dispensing probe.

Next, as shown in FIG. 9C, only the θ1 arm 122 is rotation-driven in one direction, and the dispensing probe 124 is made into contact with the inner surface of the cylindrical structure 130 of the positioning member 129, so that the position of a point B is detected (process 403).

Figure 9D:
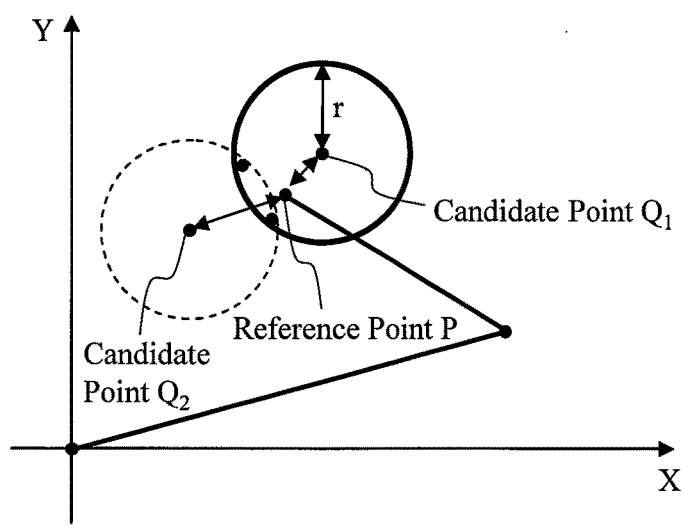
FIG. 9D is a view illustrating a step of the positioning process that is performed based on a plurality of contact points and the movement trajectory of a dispensing probe.

Through the aforementioned steps, two points that are the point A and the point B on the inner surface (i.e., the inner circumference) of the cylindrical structure 130 that constitutes the positioning member 120 are detected. Herein, when the radius r of the cylindrical structure 130 is considered, candidate points of the target point Q for positioning will be two points that are a point $Q_1$ and a point $Q_2$ as shown in FIG. 9D (process 404). This is because there are two circles that pass through the two points that are in contact with the inner sides of the circles. It should be noted that in Embodiment 1, three points on the circumference of the circle are detected, and thus, the coordinate points of the target point Q are uniquely determined At this stage, the control unit 111 calculates the distance ($PQ_1$) between the reference point P and the point $Q_1$ and the distance ($PQ_2$) between the reference point P and the point $Q_2$, and compares each of the distances with the radius r of the cylindrical structure 130 (process 405 and process 407). In FIG. 9D, $PQ_1 \leq r$ and $PQ_2 > r$. Thus, a negative result is obtained in process 405, while a positive result is obtained in process 407. In this case, the control unit 111 proceeds to process 408, and determines the candidate point $Q_1$ as the target point Q.

This is because when the cylindrical structure 130 having the point $Q_2$ as the center is considered, the reference point P is outside the inner portion of the cylindrical structure 130, and thus, when the trajectory of the dispensing probe 124 is considered, the point $Q_2$ cannot be the target point Q for positioning. Thus, in this case, the point $Q_1$ can be determined as the target point Q for positioning as described above. It should be noted that when a positive result is obtained in process 405, the control unit 111 proceeds to process 406, and determines the candidate point $Q_2$ as the target point Q.

Next, a case where candidate points for positioning cannot be identified even when the movement trajectory is taken into consideration will be described. FIGS. 10A to 10D correspond to the processes of the previously described processes 400 to 404. Thus, the processes heretofore are the same procedures as those in the aforementioned example.

Figure 10A:
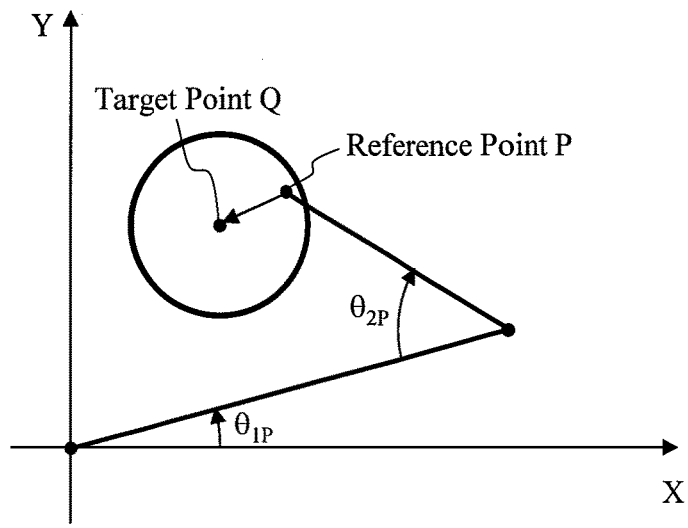
FIG. 10A is a view illustrating a step of the positioning process that is performed based on a plurality of contact points and the movement trajectory of a dispensing probe.
Figure 10B:
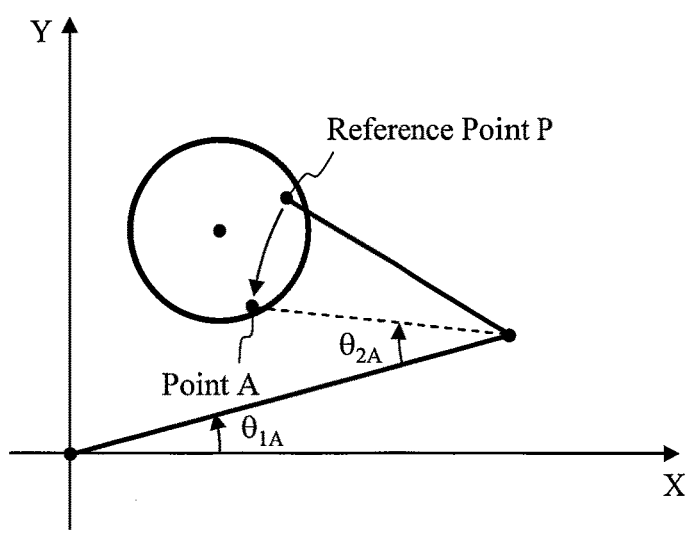
FIG. 10B is a view illustrating a step of the positioning process that is performed based on a plurality of contact points and the movement trajectory of a dispensing probe.
Figure 10C:
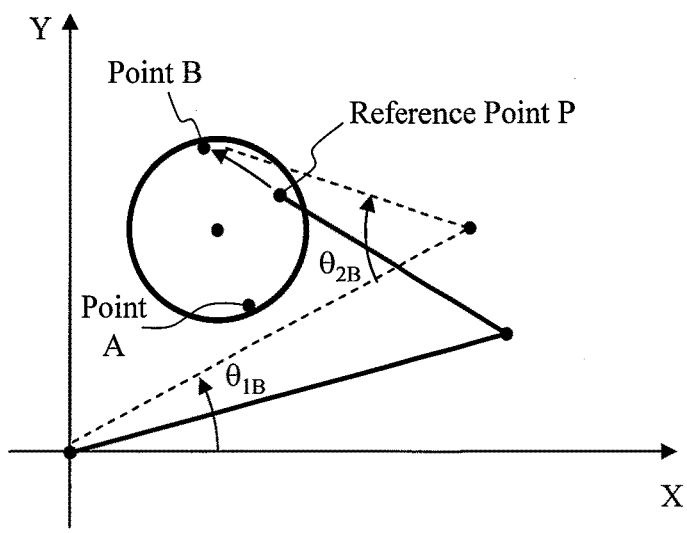
FIG. 10C is a view illustrating a step of the positioning process that is performed based on a plurality of contact points and the movement trajectory of a dispensing probe.
Figure 10D:
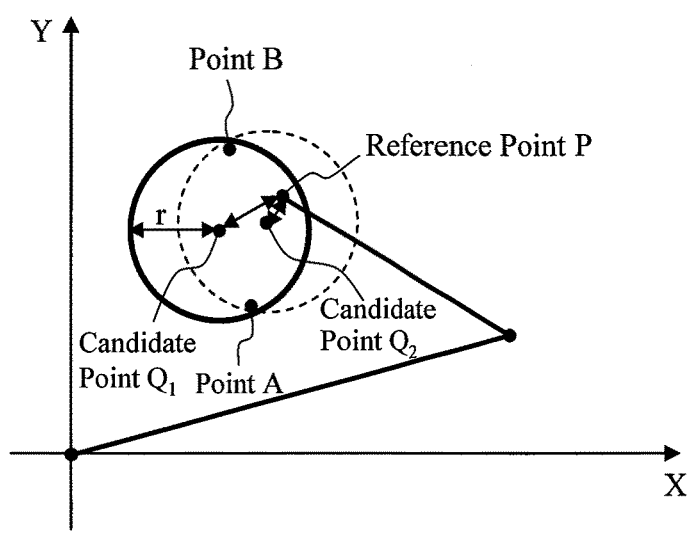
FIG. 10D is a view illustrating a step of the positioning process that is performed based on a plurality of contact points and the movement trajectory of a dispensing probe.
Figure 10E:
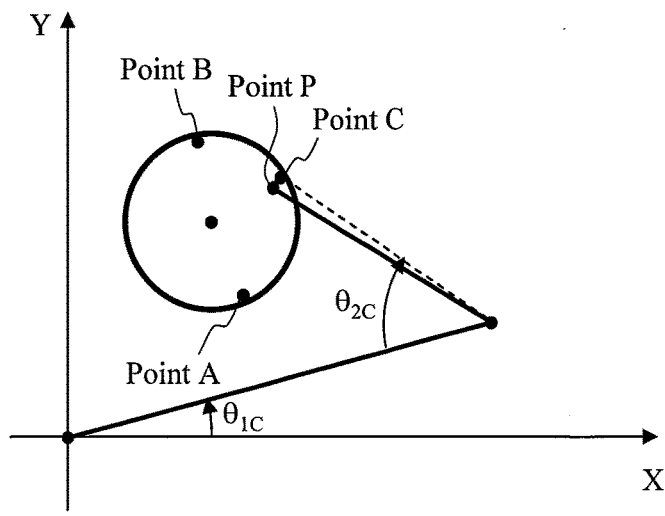
FIG. 10E is a view illustrating a step of the positioning process that is performed based on a plurality of contact points and the movement trajectory of a dispensing probe.
Figure 10F:
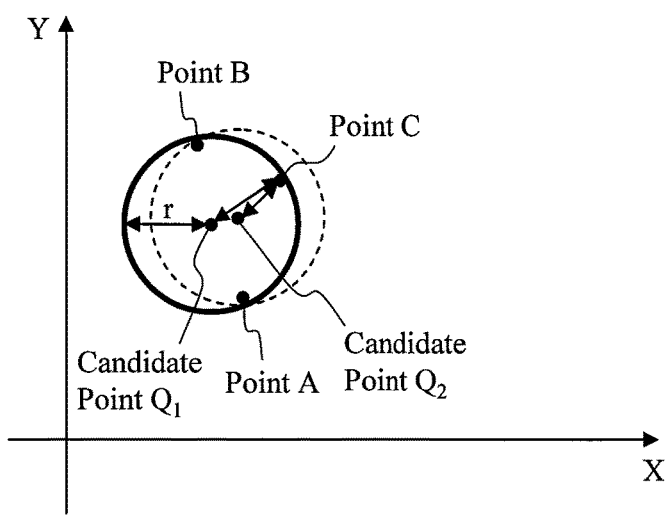
FIG. 10F is a view illustrating a step of the positioning process that is performed based on a plurality of contact points and the movement trajectory of a dispensing probe.

However, in the example of FIG. 10D, $PQ_1 \leq r$ and $PQ_2 \leq r$. Thus, a negative result is obtained in each of processes 405 and 407. That is, even when the movement trajectory of the dispensing probe 124 is taken into consideration, there is a possibility that both the point $Q_1$ and the point $Q_2$ may become the target point Q at this point in time.

In such a case, the control unit 111 rotation-drives only the θ1 arm 122 in a direction opposite to the direction in process 403, and returns the dispensing probe 124 to the reference point P. After that, the control unit 111 rotation-drives only the θ2 arm 123 in a direction opposite to the direction in process 401, and detects the third point C (processes 409 and 410).

At this point in time, only one circle that passes through the three points A, B, and C is determined. Accordingly, the coordinates of the target point Q are calculated from the three points (process 411). Herein, as a method of calculating the coordinates of the target point Q, it is possible to use either a determination method that is based on which of the distance $CQ_1$ between the candidate point $Q_1$ and the point C and the distance $CQ_2$ between the candidate point $Q_2$ and the point C coincides with the radius r, or a method of calculating the coordinates of the target point Q from the coordinates of the points A to C as in Embodiment 1.

Embodiment 4

This embodiment will describe a process for when the dispensing probe 124 is positioned at a plurality of stop positions. Herein, the process will be described with reference to FIGS. 11A to 11E. FIGS. 11A to 11E show a case where nine suction positions $T_{a1}$ to $T_{c3}$ are provided on the reagent disc 103. Typically, relative position errors of the suction positions $T_{a1}$ to $T_{c3}$ that are provided on an integral structure like the reagent disc 103 are small, while the positional relationship between different mechanisms like the reagent disc 103 and the reagent dispensing mechanism 107 often has many errors.

When relative position errors of the suction positions $T_{a1}$ to $T_{c3}$ are sufficiently smaller than errors that are allowable in the positioning process, it is possible to, as long as two of the nine suction positions can be accurately determined, execute positioning of the remaining seven suction positions through computation. Hereinafter, the method therefor will be described with reference to FIGS. 11A to 11E.

Figure 11A:
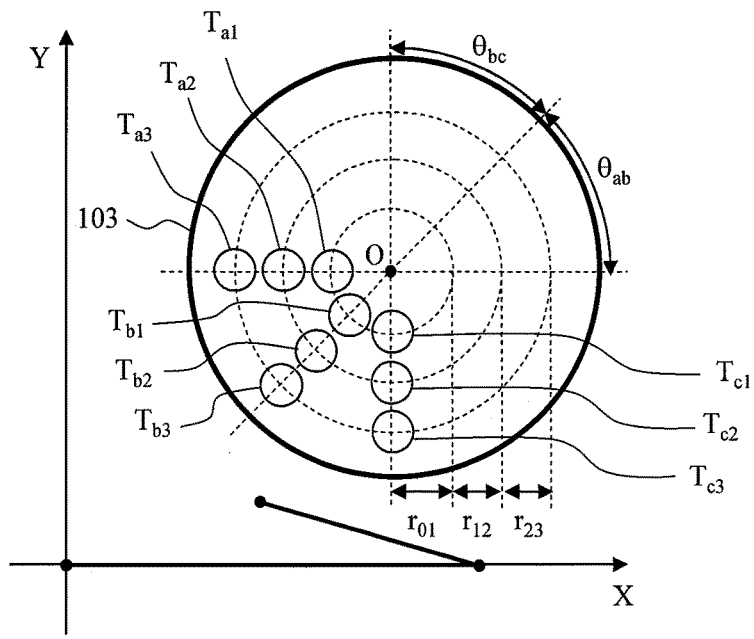
FIG. 11A is a view illustrating a step of performing a positioning process at a plurality of stop positions.

FIG. 11A shows an exemplary arrangement of the nine suction points provided on the reagent disc 103. In FIG. 11A, the nine suction positions are arranged in a dispersed manner in three rows that radially extend from the center O of the reagent disc 103. In this example, three suction positions are arranged in each row. That is, the suction positions are dispersed as a suction position row of $T_{a1}$ to $T_{a1}$, a suction position row of $T_{b1}$ to $T_{b3}$, and a suction position row of $T_{c1}$ to $T_{c3}$. It should be noted that the three suction positions that constitute each row are arranged concentrically with respect to the respective corresponding suction positions in the other suction position rows.

It should be noted that in this embodiment, it is assumed that the angles $\theta_{ab}$ and $\theta_{bc}$ between the adjacent suction position rows, as well as the distances $r_{01}$ to $r_{23}$ between the adjacent suction positions arranged in the same suction position row are known in advance.

In this embodiment, one of the three suction position rows is focused, and a process of positioning the dispensing probe 124 is actually executed only at two points in the suction position row. It should be noted that in order to minimize the relative position errors, a suction position row that is located in the middle of the three suction position rows is focused herein.

Figure 11B:
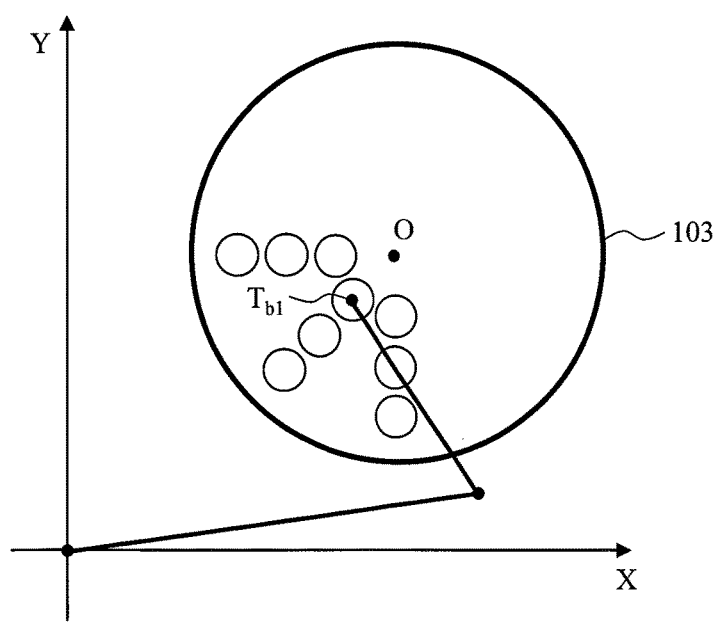
FIG. 11B is a view illustrating a step of performing a positioning process at a plurality of stop positions.

First, the control unit 111, as shown in FIG. 11B, positions the dispensing probe 124 at the innermost suction position $T_{b1}$, and calculates the position coordinates thereof. Needless to say, the processing method of Embodiment 1 or 3 described above is applied in the positioning process. However, when the dispensing drive mechanism corresponds to that of Embodiment 2, the processing method described in the embodiment is applied.

Figure 11C:
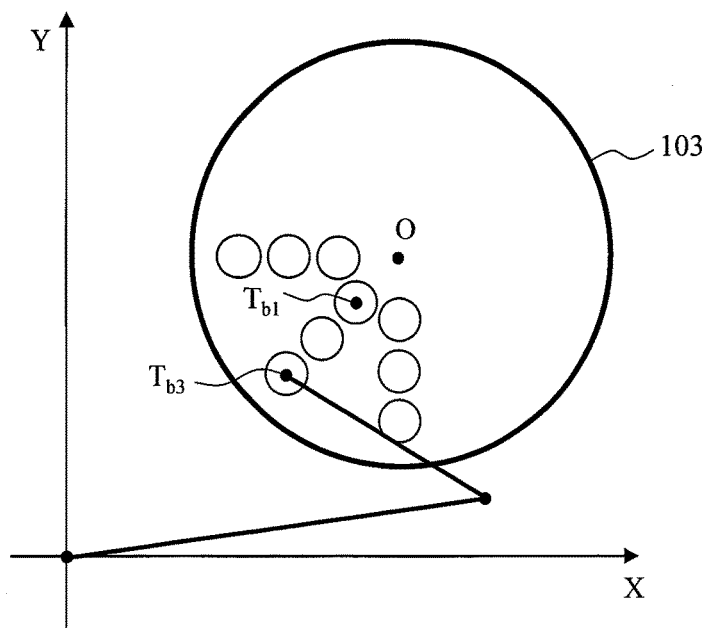
FIG. 11C is a view illustrating a step of performing a positioning process at a plurality of stop positions.
Figure 11D:
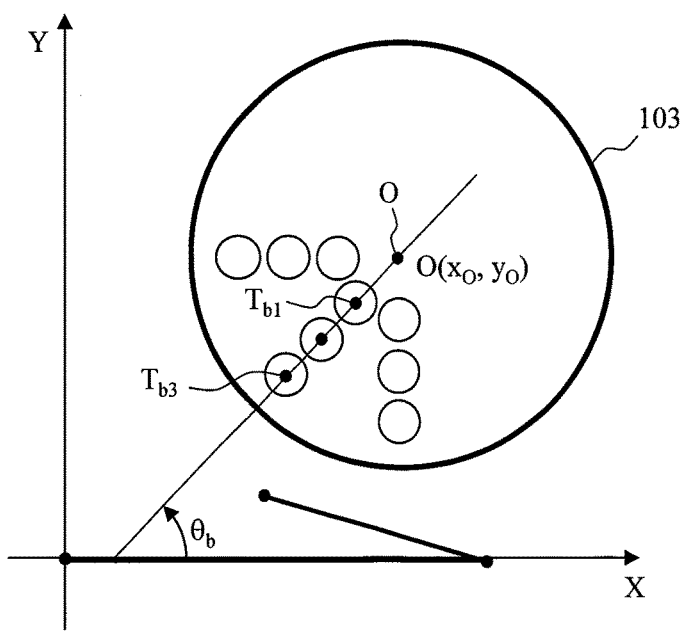
FIG. 11D is a view illustrating a step of performing a positioning process at a plurality of stop positions.

Next, the control unit 111, as shown in FIG. 11C, positions the dispensing probe 124 at the outermost suction position $T_{b3}$ that is in the same row as the suction position $T_{b1}$, and calculates the coordinate positions thereof. After that, the control unit 111, as shown in FIG. 11D, calculates the angle $\theta_b$ between a straight line, which connects the three suction positions $T_{b1}$ to $T_{b3}$ located in the same row, and the x-axis, the coordinates 0 $(x_0,y_0)$ of the center O, and the coordinates of the suction position $T_{b2}$, on the basis of the relationship between the coordinates of the suction positions $T_{b1}$ and $T_{b3}$ and the distances $r_{01}$ to $r_{23}$.

Figure 11E:
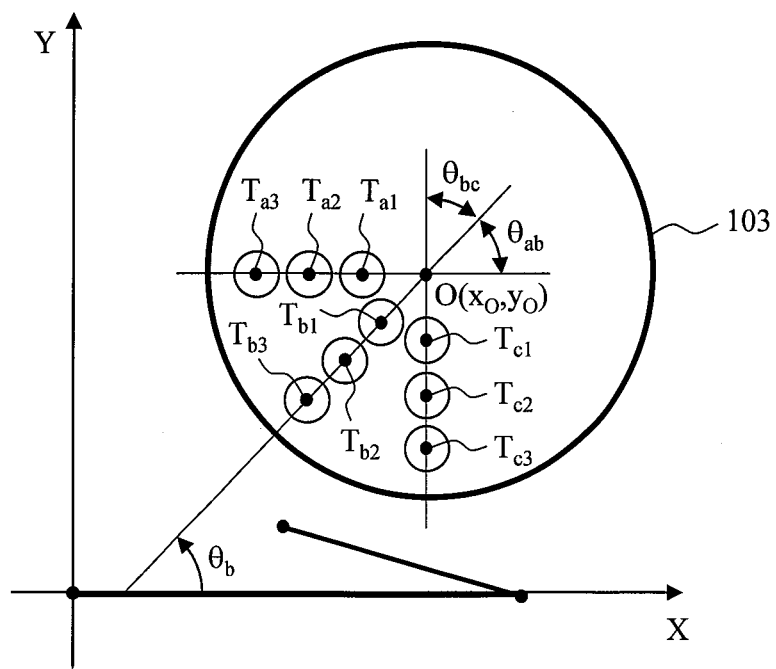
FIG. 11E is a view illustrating a step of performing a positioning process at a plurality of stop positions.

Further, the control unit 111, as shown in FIG. 11E, calculates the coordinates of the three suction positions $T_{a1}$ to $T_{a1}$ and $T_{c1}$ to $T_{c3}$ corresponding to each suction position row on the basis of the angles $\theta_{ab}$ and $\theta_{bc}$ between the suction position row for which positioning has been previously completed and the suction position rows located on the right and left sides thereof. As described above, even when positioning at a plurality of suction positions is necessary, if information about the mutual positional relationship is available, it is possible to execute, as long as the actual positioning process is executed at the minimum required suction positions $T_{b1}$ and $T_{b3}$ (i.e., two positions in this embodiment) required from the positional relationship, positioning of the remaining suction positions through a computation processes.

In this embodiment, the actual positioning process is performed at two suction positions that are the innermost suction position and the outermost suction position among the three suction positions arranged in the same row. However, the actual positioning may be performed at any two points located in the same row.

Other Embodiments

The previous embodiments have described cases where the shape of a portion, which is contacted by the dispensing probe 124, of the positioning member 129 is the cylindrical structure 130. However, the conditions that are necessary to apply the processing method described in the previous embodiments are that the inner surface should be circular in shape in the XY plane. Thus, the outer surface need not necessarily be circular in shape. That is, the outer surface need not have the cylindrical structure 130.

Meanwhile, when positioning is executed by using contact with the outer surface of the positioning member 129, it is acceptable as long as the outer surface of the positioning member 129 that is contacted by the dispensing probe 124 is circular in shape in the XY plane. That is, the shape of a portion that is actually contacted by the dispensing probe 124 may be cylindrical in shape. Even in such a case, the center coordinates of the positioning member 129 may be calculated through calculation of the coordinates of two or more contact points with the outer surface.

It should be noted that the present invention is not limited to the aforementioned embodiments, and includes various variations. For example, although the aforementioned embodiments have been described in detail to clearly illustrate the present invention, the present invention need not include all of the structures described in the embodiments. It is possible to replace a part of a structure of an embodiment with a structure of another embodiment. In addition, it is also possible to add, to a structure of an embodiment, a structure of another embodiment. Further, it is also possible to, for a part of a structure of each embodiment, add/remove/substitute a structure of another embodiment.

Some or all of the aforementioned structures, functions, processing units, processing means, and the like may be implemented as an integrated circuit or other hardware, for example. Alternatively, each of the aforementioned structures, functions, and the like may be implemented through analysis and execution of a program that implements each function by a processor. That is, each of the aforementioned structures, functions, and the like may also be implemented as software. Information such as the program that implements each function, tables, and files can be stored in a storage device such as memory, a hard disk, or a SSD (Solid State Drive); or a storage medium such as an IC card, an SD card, or a DVD.

In addition, the control lines and information lines represent those that are considered to be necessary for the description, and do not necessarily represent all control lines and information lines that are necessary for a product. Thus, in practice, almost all structures may be considered to be mutually connected.

REFERENCE SIGNS LIST

100 Sample cup
101 Sample rack
102 Reagent bottle
103 Reagent disc
104 Cell
105 Cell disc
106 Sample dispensing mechanism
107 Reagent dispensing mechanism
108 Agitation unit
109 Measuring unit
110 Cleaning unit
111 Control unit
112 Data storage unit
113 Input unit
114 Measuring unit
115 Analytical unit
116 Output unit
121 Shaft
122 θ1 arm
123 θ2 arm
124 Dispensing probe
125 Plunger
126 Shaft
127 Plunger
128 Liquid level detector
129 Positioning member
130 Cylindrical structure
131 Dent

The invention claimed is:

1. An automatic analytical method executed with an automatic analytical device, the automatic analytical device comprising:
 a cell for holding a sample or a reagent,
 a positioning member configured to attach to an open portion of the cell, the positioning member having a cylindrical portion,
 a dispensing probe drive mechanism, comprising:
 a vertical shaft,
 a first rotational drive shaft rotatably attached to the vertical shaft,
 a second rotational drive shaft rotatably attached to the first rotational drive shaft,
 a dispensing probe, connected to the second rotational drive shaft, that dispenses a predetermined amount of the sample or the reagent into the cell, and
 a contact detection mechanism that detects that the dispensing probe has come into contact with the positioning member,
wherein the first and second rotational drive shafts move the dispensing probe two-dimensionally in a horizontal direction, and
wherein the automatic analytical device further comprises a control unit that controls the dispensing probe drive mechanism and the contact detection mechanism, the method comprising causing the control unit to perform:
drive-controlling rotation of the first and second rotational drive shafts of the dispensing probe drive mechanism so as to cause the dispensing probe to move to an initial position;
drive-controlling rotation of only the second rotational drive shaft of the dispensing probe drive mechanism with respect to the first rotational drive shaft so as to cause the dispensing probe move from the initial position to contact an inner surface of the cylindrical portion of the positioning member at a first position and calculating position information of the first position;
after causing the dispensing probe to contact the inner surface of the cylindrical portion at the first position, drive-controlling rotation of only the second rotational drive shaft of the dispensing probe drive mechanism with respect to the first rotational drive shaft so as to cause the dispensing probe to contact an inner surface of the cylindrical portion of the positioning member at a second position and calculating position information of the second position;
after causing the dispensing probe to contact the inner surface of the cylindrical portion at the second position, drive-controlling rotation of only the second rotational drive shaft of the dispensing probe drive mechanism so as to cause the dispensing probe to return to the initial position;
after causing the dispensing probe to return to the initial position, drive-controlling rotation of only the first rotational drive shaft with respect to the vertical shaft so as to cause the dispensing probe to contact the inner surface of the cylindrical portion of the positioning member at a third position and calculating position information of the third position; and
calculating position information on a center position of the cell on the basis of the position information of the first, second, and third positions by performing the steps of:
selecting a first pair of positions from the first, second and third positions;
selecting a second pair of positions from the first, second and third positions; the second pair being different from the first pair;
calculating a first perpendicular bisector perpendicularly bisecting a first line connecting the first pair of positions;
calculating a second perpendicular bisector perpendicularly bisecting a second line connecting the second pair of positions; and
calculating an intersection of the first and second perpendicular bisectors; and
corresponding the intersection to the center point of the cell.

* * * * *